United States Patent [19]

Booth et al.

[11] 4,283,543
[45] Aug. 11, 1981

[54] PROCESS FOR PREPARING THE COMPOUND 5-T-BUTYL-2-METHYLAMINO-1,3,4-TRIADIAZOLE

[75] Inventors: David L. Booth; Richard M. Rodebaugh, both of Crystal Lake, Ill.

[73] Assignee: Morton-Norwich Products, Inc., Chicago, Ill.

[21] Appl. No.: 86,414

[22] Filed: Oct. 19, 1979

[51] Int. Cl.³ .......................................... C07D 285/12
[52] U.S. Cl. .................................................... 548/138
[58] Field of Search ........................................ 548/138

[56] References Cited

U.S. PATENT DOCUMENTS

| | | | |
|---|---|---|---|
| 3,887,572 | 6/1975 | Tao | 548/138 |
| 4,086,077 | 4/1978 | Doyle | 548/138 |

Primary Examiner—Alton D. Hollins
Attorney, Agent, or Firm—Jack Axelrood

[57] ABSTRACT

A process for preparing the compound 5-t-butyl-2-methylamino-1,3,4-thiadiazole,

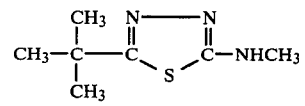

in high yield by the reaction of 4-methyl-3-thiosemicarbazide with pivalic acid in a solution containing both polyphosphoric acid and concentrated sulfuric acid, followed by neutralizing the reaction mixture with a neutralizing mixture comprising an organic solvent and an alkaline substance dissolved in water and separating 5-t-butyl-2-methylamino-1,3,4-thiadiazole from the organic phase.

25 Claims, No Drawings

PROCESS FOR PREPARING THE COMPOUND 5-T-BUTYL-2-METHYLAMINO-1,3,4-TRIADIAZOLE

BACKGROUND OF THE INVENTION

The field of this invention, in general, is that of improved methods for preparing well-known organic intermediates which are used in the preparation of end products having a variety of useful properties. In view of the fact that many chemical reactions for the preparation of useful end-product compounds proceed through the formation of intermediates, it, therefore, becomes important to develop increasingly efficient methods for the synthesis of such intermediates.

More particularly, this invention relates to the novel preparation in high yield of the compound 5-t-butyl-2-methylamino-1,3,4-thiadiazole, one use of which is to prepare the broad spectrum herbicide N-[5-(1,1-dimethylethyl)-1,3,4-thiadiazol-2-yl]-N,N'-dimethylurea, known in commerce under the common name Tebuthiuron. U.S. Pat. No. 3,803,164 discloses the preparation of certain herbicidally active compounds, the 1-(5-alkylthiadiazol-2-yl)-1,3-dialkylureas, of which Tebuthiuron is a member, by the reaction of a 2-alkylamino-5-alkyl-1,3,4-thiadiazole with an isocyanate of the formula R—N=C=O where R is hydrogen or $C_1$-$C_4$ alkyl.

The compound 5-t-butyl-2-methylamino-1,3,4-thiadiazole can also be utilized as the starting material in a wide variety of reactions to provide useful end products, such as, for example, in the reaction with isocyanates to form ureas, with isothiocyanates to form thioureas, with organic acids and acid chlorides to form amides, with alkyl and aryl chloroformates to form carbamates, and with alkyl chlorides to form alkylated amines.

SUMMARY OF THE INVENTION

The present invention relates to an efficient process for preparing the compound 5-t-butyl-2-methylamino-1,3,4-thiadiazole in high yield comprising:

(i) adding 4-methyl-3-thiosemicarbazide to a solution of pivalic acid to form a slurry in a first vessel;

(ii) placing a solution comprising polyphosphoric acid and concentrated sulfuric acid in a second vessel;

(iii) feeding the contents of said first and second vessels concomitantly into a third vessel while agitating and maintaining the temperature of the resultant mixture at a maximum of about 90° C. to form 5-t-butyl-2-methylamino-1,3,4-thiadiazole;

(iv) neutralizing said mixture with a neutralizing agent comprising an organic solvent and an alkaline substance dissolved in water to form an essentially neutralized two-phase, water-organic solvent system; and (v) separating from the neutralized system of (iv) an organic phase and recovering the compound 5-t-butyl-2-methylamino-1,3,4-thiadiazole therefrom.

The yield of 5-t-butyl-2-methylamino-1,3,4-thiadiazole by the present process is virtually 100% of theoretical, ranging from about 98% to close to 100%.

For convenience in manufacturing 5-t-butyl-2-methylamino-1,3,4-thiadiazole, a "heel" may be employed. The term "heel" refers to a previously formed mixture comprising 5-t-butyl-2-methylamino-1,3,4-thiadiazole, polyphosphoric and sulfuric acids and solvent, all of which result from the reaction of 4-methyl-3-thiosemicarbazide with pivalic acid in the presence of an organic solvent and a solution containing both polyphosphoric acid and concentrated sulfuric acid. This heel, so formed, is used as the reaction medium into which are fed concurrent streams of the two reactants which formed the heel in the first instance, i.e. (1) a slurry comprising 4-methyl-3-thiosemicarbazide and a solution of pivalic acid, and (2) a solution comprising polyphosphoric acid and concentrated sulfuric acid. The use of a heel in the present process contributes to the overall efficiency of the process as it serves as a reaction medium which permits a more effective temperature control by inhibiting any excessive temperature rise caused by the admixture of the reactants. The heel is used conveniently in a quantity which may vary from about ten to about forty percent by weight of the overall weight of the reactants.

A portion of the reaction mixture formed in step (iii) of the present process may be used as a heel in subsequent preparations of the intermediate.

The pivalic acid may be dissolved in a solvent selected from the group consisting of aromatic and aliphatic hydrocarbons, such as, for example, benzene, toluene, xylene, heptane and hexane. Of these, toluene is preferred. Alternatively, the pivalic acid may be used in the molten state in the absence of solvent.

It has been found that the addition of the combination of pivalic acid and 4-methyl-3-thiosemicarbazide in slurry form to the heel concomitantly with the mixture of polyphosphoric and sulfuric acid is a factor which permits easy temperature control and which contributes to the excellent yields of the present process for preparing the intermediate 5-t-butyl-2-methylamino-1,3,4-thiadiazole. In the instance where a solvent solution of pivalic acid is added separately to the polyphosphoric acid and sulfuric acid mixture and later followed by the addition of the 4-methyl-3-thiosemicarbazide, the yield of the intermediate product is greatly reduced, amounting to about 62% on an overall basis. Further, where 4-methyl-3-thiosemicarbazide is first added to the polyphosphoric acid and sulfuric acid mixture, and then followed by the addition of the solution of pivalic acid, the yield of the intermediate is reduced even further than when the order is reversed.

Similarly, the separate addition of all of the polyphosphoric acid-sulfuric acid to the heel, later followed by the pivalic acid and 4-methyl-3-thiosemicarbazide reactants results in a much lower yield than when the concomitant addition of the present process is followed.

A solution containing both polyphosphoric and sulfuric acids is required in the process of this invention inasmuch as the use of each acid alone significantly lowers the yield of the intermediate product. The term "concentrated" as used herein in referring to the strength of sulfuric acid means a concentration of from about 85% to about 100% of sulfuric acid as $H_2SO_4$. The polyphosphoric acid used has a concentration of from about 110% to about 120% of polyphosphoric acid as $H_3PO_4$.

In the combination of polyphosphoric acid and sulfuric acid, the ratio of polyphosphoric acid to sulfuric acid may vary from about 2.0:1 to about 4.0:1. The preferred ratio is 3 parts of polyphosphoric acid to one part of sulfuric acid.

The temperature of the overall mixture of step (iii) may vary from about 60° C. to about 90° C., although the preferred range is from about 70° C. to about 80° C.

This preferred range is easily maintained by the use of the heel which serves to moderate the exotherm caused by the addition of the reactants, and by the concomitant addition of the reactants from two separate vessels.

DESCRIPTION OF THE PREFERRED EMBODIMENTS

Example 1

Into a first dropping funnel was placed 341.2 g. of a solution consisting of 255.9 g. of 115% polyphosphoric acid and 85.3 g. of 96.2% sulfuric acid. A second dropping funnel contained a mechanically stirred slurry of 4-methyl-3-thiosemicarbazide (88.4 g., 0.845 mole) in pivalic acid (85.93 g., 0.843 mole) and toluene (7.3 g.). The contents of the two dropping funnels were added simultaneously into a four-necked, 1-liter flask equipped with a stirrer, thermometer and a drying tube over a period of 45 minutes, the reaction temperature being maintained at 70° C.

The temperature was then increased to 80° C. and held for about 1 hour. The contents of the flask were then poured slowly into a stirred mixture of 28% aqueous ammonia (445 ml), water (210 ml) and toluene (40 ml) contained in a 2-liter beaker. The temperature was allowed to rise to 75°–80° C. and the pH of the aqueous phase was adjusted to 6.1 by the addition of 150 ml of 28% ammonia. The aqueous and organic phases were separated while hot (75° C.). The product, 5-t-butyl-2-methylamino-1,3,4-thiadiazole was isolated as a yellow to orange solid in 100% yield, melting point 78°–80° C., by evaporation of the organic phase to dryness under reduced pressure.

Example 2

Into a four-necked, 1-liter flask equipped with a stirrer, thermometer and a drying tube was charged a solution of 115% polyphosphoric acid (63.98 g) and 96.2% sulfuric acid (21.33 g). A solution of pivalic acid (21.48 g, 0.2107 mole) and toluene (1.82 g) was added followed by 4-methyl-3-thiosemicarbazide (22.1 g, 0.2102 mole). The mixture was stirred with the initial reaction exotherm being controlled with cooling if necessary such that the reaction temperature did not rise above 70° C. The reaction mixture was then maintained with stirring and heating for about 1 hour at 70° C. The reaction flask was then fitted with two dropping funnels. The first funnel contained 256 g of a solution consisting of 192 g of 115% polyphosphoric acid and 64 g of 96.2% sulfuric acid. The second funnel contained a mechanically stirred slurry of 4-methyl-3-thiosemicarbazide (66.3 g, 0.631 mole) in pivalic acid (64.45 g, 0.632 mole) and toluene (5.45 g). The contents of the two dropping funnels were added simultaneously to the stirred reaction mixture (reaction "heel") over a period of 45 minutes, the reaction temperature being maintained at 70° C. The temperature was then increased to 80° C. and held for about 1 hour. The contents of the flask were then poured slowly into a stirred mixture of 28% aqueous ammonia (445 ml), water (210 ml) and toluene (40 ml) contained in a 2-liter beaker. The temperature was allowed to rise to 75°–80° C. and the pH of the aqueous phase was adjusted to 6.1 by the addition of 150 ml of 28% ammonia. The aqueous and organic phases were separated while hot (75° C.). The product, 5-t-butyl-2-methylamino-1,3,4-thiadiazole was isolated as a yellow to orange solid in 98% yield, melting point 78°–80° C., by evaporation of the organic phase to dryness under reduced pressure.

Example 3

The procedure of Example 2 was repeated except that the intermediate 5-t-butyl-2-methylamino-1,3,4-thiadiazole was not isolated, but was allowed to remain in situ in the toluene phase. The toluene phase was diluted with an additional 262 ml of toluene, the solution was dried by azeotropic distillation, and then 58.7 g. of methyl isocyanate were added to form Tebuthiuron, N-[5-(1,1-dimethylethyl)-1,3,4-thiadiazol-2-yl]-N,N'-dimethylurea, which precipitates from the reaction mixture. The mixture was diluted with 400 ml of water, the precipitate separated by filtration and washed with 75 ml of water. Drying provided 174.3 g. of product, representing a yield of 90.8% of theoretical, based on the 4-methyl-3-thiosemicarbazide.

What is claimed is:

1. A process for preparing the compound 5-t-butyl-2-methylamino-1,3,4-thiadiazole in high yield comprising:
    (i) adding 4-methyl-3-thiosemicarbazide to a solution of pivalic acid to form a slurry in a first vessel;
    (ii) placing a solution comprising polyphosphoric acid and concentrated sulfuric acid in a second vessel;
    (iii) feeding the contents of said first and second vessels concomitantly into a third vessel while agitating and maintaining the temperature of the resultant mixture at a maximum of about 90° C. to form 5-t-butyl-2-methylamino-1,3,4-thiadiazole;
    (iv) neutralizing said mixture with a neutralizing agent comprising an organic solvent and an alkaline substance dissolved in water to form an essentially neutralized two-phase, water-organic solvent system; and
    (v) separating from the neutralized system of (iv) an organic phase and recovering the compound 5-t-butyl-2-methylamino-1,3,4-thiadiazole therefrom.

2. The process of claim 1 wherein the pivalic acid is dissolved in a solvent selected from the group consisting of aromatic and aliphatic hydrocarbons, and mixtures thereof.

3. The process of claim 1 wherein in (iii) the temperature of the overall mixture is maintained from about 70° C. to about 80° C.

4. The process of claim 1 wherein the concentration of the concentrated sulfuric acid is from about 85% to 100% as $H_2SO_4$ and the concentration of the polyphosphoric acid is from about 110% to about 120% as $H_3PO_4$.

5. The process of claim 1 wherein the ratio by weight of polyphosphoric acid to sulfuric acid is from about 2.0:1 to about 4.0:1.

6. The process of claim 1 wherein the alkaline substance of the neutralizing agent is selected from the group consisting of ammonium hydroxide, sodium hydroxide, potassium hydroxide and calcium hydroxide.

7. The process of claim 1 wherein the solvent for dissolving the pivalic acid and the organic solvent portion of the two-phase system is toluene.

8. The process of claim 1 wherein the solvent for dissolving the pivalic acid and the organic solvent portion of the two-phase system is xylene.

9. The process of claim 1 wherein the solvent for dissolving the pivalic acid and the organic solvent portion of the two-phase system is benzene.

10. The process of claim 1 wherein the solvent for dissolving the pivalic acid is hexane.

11. The process of claim 1 wherein the solvent for dissolving the pivalic acid is heptane.

12. The process of claim 1 wherein in (i) the 4-methyl-3-thiosemicarbazide is added to molten pivalic acid to form a slurry in a first vessel.

13. A process for preparing the compound 5-t-butyl-2-methylamino-1,3,4-thiadiazole in high yield comprising:
  (i) adding 4-methyl-3-thiosemicarbazide to a solution of pivalic acid to form a slurry in a first vessel;
  (ii) placing a solution comprising polyphosphoric acid and concentrated sulfuric acid in a second vessel;
  (iii) feeding the contents of said first and second vessels concomitantly into a third vessel containing a heel, i.e., a reacted mixture having been formed previously by reacting 4-methyl-3-thiosemicarbazide with a solution of pivalic acid in the presence of a solution containing concentrated polyphosphoric acid and concentrated sulfuric acid to form 5-t-butyl-2-methylamino-1,3,4-thiadiazole in situ;
  (iv) agitating and maintaining the temperature of the overall mixture of (iii) at a maximum of about 90° C., said overall mixture becoming enriched with respect to 5-t-butyl-2-methylamino-1,3,4-thiadiazole;
  (v) admixing the overall enriched mixture of (iv) with a neutralizing mixture comprising an organic solvent and an alkaline substance dissolved in water to form an essentially neutralized two-phase, water-organic solvent system; and
  (vi) separating from the neutralized system of (v) an organic phase and recovering the compound 5-t-butyl-2-methylamino-1,3,4-thiadiazole therefrom.

14. The process of claim 13 wherein a portion of the contents of the reaction mixture of (iii) is used as the heel in (iii).

15. The process of claim 13 wherein the pivalic acid is dissolved in a solvent selected from the group consisting of aromatic and aliphatic hydrocarbons, and mixtures thereof.

16. The process of claim 13 wherein in (iv) the temperature of the overall mixture is maintained from about 70° C. to about 80° C.

17. The process of claim 13 wherein the concentration of the concentrated sulfuric acid is from about 85%–100% as $H_2SO_4$ and the concentration of the concentrated polyphosphoric acid is from about 110 to about 120% as $H_3PO_4$.

18. The process of claim 13 wherein the ratio by weight of polyphosphoric acid to sulfuric acid is from about 2.0:1 to about 4.0:1.

19. The process of claim 13 wherein the alkaline substance of the neutralizing mixture is selected from the group consisting of ammonium hydroxide, sodium hydroxide, potassium hydroxide and calcium hydroxide.

20. The process of claim 13 wherein the solvent for dissolving the pivalic acid and the organic solvent portion of the two-phase system is toluene.

21. The process of claim 13 wherein the solvent for dissolving the pivalic acid and the organic solvent portion of the two-phase system is xylene.

22. The process of claim 13 wherein the solvent for dissolving the pivalic acid and the organic solvent portion of the two-phase system is benzene.

23. The process of claim 13 wherein the solvent for dissolving the pivalic acid is hexane.

24. The process of claim 13 wherein the solvent for dissolving the pivalic acid is heptane.

25. The process of claim 13 wherein in (i) the 4-methyl-3-thiosemicarbazide is added to molten pivalic acid to form a slurry in a first vessel.

* * * * *

UNITED STATES PATENT AND TRADEMARK OFFICE
CERTIFICATE OF CORRECTION

PATENT NO. : 4,283,543

DATED : August 11, 1981

INVENTOR(S) : David L. Booth and Richard M. Rodebaugh

It is certified that error appears in the above-identified patent and that said Letters Patent are hereby corrected as shown below:

IN THE TITLE, CHANGE "TRIADIAZOLE" to "THIADIAZOLE".

Signed and Sealed this

Tenth Day of November 1981

[SEAL]

Attest:

GERALD J. MOSSINGHOFF

*Attesting Officer*  *Commissioner of Patents and Trademarks*